United States Patent [19]

Akopov et al.

[11] 3,949,923

[45] Apr. 13, 1976

[54] SURGICAL SUTURING INSTRUMENT

[76] Inventors: Ernest Mikhailovich Akopov, Dubninskaya ulitsa, 61, kv. 88; Nikolai Nikolaevich Kapitanov, 8 ulitsa Oktyabrskogo polya, 5, kv. 9; Alexei Alexeevich Strekopytov, ulitsa Vsevoloda Vishnevskogo, 10, kv. 67; Evgenia Sergeevna Ogoltsova, Rogozhsky val, 13, korpus 3, kv. 14; Alexandr Ilich Paches, ulitsa Medvedeva, 12/6, kv. 5, all of Moscow, U.S.S.R.

[22] Filed: June 5, 1974

[21] Appl. No.: 476,558

[30] Foreign Application Priority Data

July 26, 1973 U.S.S.R............................. 1954520

[52] U.S. Cl. ................................................. 227/19
[51] Int. Cl.²......................................... B25C 5/02
[58] Field of Search ........................................ 227/19

[56] References Cited
UNITED STATES PATENTS

| | | | |
|---|---|---|---|
| 3,494,533 | 2/1970 | Green et al. | 227/19 |
| 3,589,589 | 6/1971 | Akopov | 227/19 |
| 3,692,224 | 9/1972 | Astafieu et al. | 227/19 |

*Primary Examiner*—Granville Y. Custer, Jr.
*Attorney, Agent, or Firm*—Holman & Stern

[57] ABSTRACT

A surgical instrument for suturing organs and tissues with metal staples which includes a supporting body with a longitudinal slot and a flat frame. The frame has a supporting jaw provided with a flat face facing the slot. The flat face of the supporting jaw has a number of depressions for the staple legs to bend. The slot accommodates the staple body with the head into which the staple magazine is inserted, and a staple ejector. The slot in the supporting body opens in a direction perpendicular to the plane of the supporting body frame, whereby it becomes possible for the staple body with the staple ejector to be inserted into and extracted from the slot in said direction.

8 Claims, 13 Drawing Figures

SURGICAL SUTURING INSTRUMENT

BACKGROUND OF THE INVENTION

The present invention relates to medical equipment and has particular reference to surgical suturing instruments. The disclosed instrument can find application for example in oncological practice for suturing the walls of the pharynx upon laryngectomy for cancer, as well as for suturing organs and tissues of the thoracic and abdominal cavities, e.g. for suturing pulmonary tissues.

Known in the art is a surgical suturing instrument, comprising a supporting body with a slot and a hook-shaped frame (cf. USSR Inventor's Certificate No. 125,523). The frame has a supporting jaw arranged transversely with respect to said slot and has an oblong flat area provided with depressions for staple legs to be bent. The slot in the supporting body opens in the direction parallel to the plane of the supporting body frame. Said slot accommodates a stapler body with the head into which a stapler magazine is inserted, said staple body being free to travel lengthwise in said slot. A staple ejector is housed in the stapler body with the capacity to traverse the stapler body. Because said slot in the supporting body is arranged with its open end in the direction parallel to the plane of the supporting body frame, the stapler body can be inserted into the slot and removed therefrom only in said direction.

When the stapler body is placed in the working position with respect to the supporting body, the gap between the supporting jaw and the staple magazine corresponds to the thickness of the tissues being sutured. When the stapler body is in the initial position, the stapler body can be inserted into the slot of the supporting body or withdrawn therefrom. To insert the stapler body into the slot of the supporting body in the initial position of the former more room than the above mentioned gap is needed in the direction of the plane of the frame.

The stapler body and the staple ejector are provided with corresponding actuators which traverse the supporting body towards the supporting jaw.

The staple magazine has open-end slots to accommodate metal staples therein. The slots are arranged in a strict correspondence with the depressions in the frame supporting jaw. The staple ejector has driving projections arranged correspondingly to the magazine slots. When the ejector moves towards the frame supporting jaw, its driving projections enter the magazine slots to eject the staples therefrom.

To prevent the tissue or organ being sutured from slipping off the instrument, the stapler head is provided with a fork limiter.

During suturing with the use of the above-discussed instrument, the tissue or organ being sutured is placed in between the flat area of the supporting jaw and the working end of the staple magazine facing said flat area. The tissue or organ being sutured may be placed into such a position by being introduced through the side opening of the hook-shaped frame. Then, the tissue or organ undergoing suturing is fixed in position by the fork limiter, whereupon the surgeon operates the actuator of the stapler body, thus positioning the magazine with respect to the supporting jaw of the supporting body such that the necessary suturing gap is established in between the flat area of the supporting jaw and the magazine. Next, the tissues are sutured by operating the staple ejector actuator, with the result that the ejector projections pass through the magazine slots and drive the staples out. The staple legs pierce the tissues being sutured and are thrust against the depressions in the flat area of the supporting jaw thereby bending and thus suturing the tissues. The tissue to be excised is cut out, the magazine is withdrawn from the supporting jaw, and the instrument is removed from the operative wound.

However, the known instrument is inconvenient or impractical to be used for suture application in places of difficult accessibility or under specific conditions, where the space for manipulations involved in setting the instrument into the suturing position is limited, especially in the plane of the frame. This disadvantage is due to the construction of the supporting body of the instrument, wherein the supporting jaw of the supporting body and the staple magazine can be brought into position to the tissues being sutured, only through the side opening of the hook-shaped frame of the supporting body. For the supporting jaw and the staple magazine to be set into the suturing position using said technique, both of them must be moved with respect to the tissues undergoing suturing through a distance equal to the width of the supporting body frame. If the space in the operative wound proves to be insufficient, the surgeon has to perform complicated manipulations with the instrument to avoid any injury that is liable to be inflicted upon both the tissues being sutured and the surrounding tissues.

To cite an example, in the case of laryngectomy for cancer, by resorting to the known instrument, the frame supporting jaw and the staple magazine can be brought under the tumor to be excised to the place of suture application to the pharynx only from the direction of the chin or the breast which are located much superior to the place of suture application. Moreover, this involves some complicated tissue-injuring manipulations in a narrow space confined between the tumor resected on the side of the chin and in the region of the trachea, and the remaining organs and tissues of the patient's head and neck.

Another disadvantage inherent in the known instrument resides in large cross-sectional dimensions of the frame elements necessary for imparting reasonable rigidity to the construction of the instrument which has to sustain considerable loads resulting from staple deformation during suturing process. This feature restricts the field of application of the instrument. Thus, the application of the instrument involves relatively wide portions of the tissues being sutured which are required to be forced in between the frame supporting jaw and the staple magazine. This increases the distance from the line of staples of the suture to the plane of cut of the tissues and results in rougher suture scar. Additionally, a larger space is required between the tissues in order to initially position the supporting jaw and the side web of the supporting body frame. In some cases such favourable conditions cannot be provided and the apparatus is inapplicable.

To exemplify this statement, in the case of laryngectomy for cancer the cross-sectional dimension of the side web of the frame is too large and interferes with its positioning in the incision made in the tissues in the region of the chin or the trachea; the width of the supporting jaw is too large and makes it less practicable to place the jaw upon the healthy but narrow portions of the pharynx. This results in a reduced lumen of the sutured pharynx.

Simply reducing the cross-sectional dimensions of the frame elements of the supporting body makes it impossible to use the known instrument in any other application technique reasonable for the operation under discussion. For instance, the known instrument could be positioned, in principle, to the place of suture application from above (with respect to the patient in recumbent position) rather than from the chin or the breast, so as to pass the conglomerate of the tumor tissues through the gap between the supporting jaw and the magazine in the direction perpendicular to the plane of the frame. However, this cannot be carried out with the known instrument, since the distance from the supporting jaw to the magazine is much less than the size of the conglomerated tumor tissues. Therefore, the latter cannot be passed through the gap between the supporting jaw and the magazine. Any increase of said gap is self-defeating since it would necessitate an increase in the length of the side web of the supporting body hook and result in a reduced rigidity of the supporting body. Consequently, an inferior quality of sutures would result. To maintain adequate rigidity of the instrument in this case, it is necessary to increase the cross-sectional dimensions of the hook web which renders the known instrument still less applicable for the purpose.

OBJECTS AND SUMMARY OF THE INVENTION

It is an object of the present invention to provide a surgical suturing instrument which is capable of applying sutures in places of difficult accessibility or under specific conditions where there is restricted room for manipulations indispensable in setting the instrument into suturing position.

It is another object of the present invention to provide a surgical instrument which is capable of being positioned at the site of tissues needing suturing without any injury inflicted thereupon.

It is another object of the present invention to provide a surgical instrument capable of applying a suture of an improved quality.

It is another object of the present invention to provide a surgical instrument capable of attaining an increased lumen of tubular organs when applying a longitudinal lateral suture to the wall thereof.

Said objects are accomplished in a surgical suturing instrument, comprising a supporting body with a slot and a flat frame having a supporting jaw arranged transversely with respect to the slot and provided with a flat face facing the slot and carrying depressions for stapler legs to bend, a staple body mounted in said slot of the supporting body with the capacity to longitudinally transverse said slot and incorporating a head, a staple magazine accommodated in the stapler body head, a staple ejector associated with the body with the capacity to longitudinally transverse said body stapler, and actuators of the stapler body and of the staple ejector. According to the invention, said slot in the supporting body opens in the direction perpendicular to the plane of the supporting body frame, so as to provide for the stapler body with the ejector to be inserted into and extracted from the slot in said direction.

It is desirable that the frame of the supporting body be made closed and have two webs parallel to the slot which serve as guides for the head of the stapler body, said webs being provided with recesses located in their rear portions (with respect to the supporting jaw), which recesses are commensurable in length with the head of the stapler body and are adapted to provide for the stapler body with the ejector to be inserted into the slot of the supporting body and withdrawn therefrom when in the rearmost position with respect to the supporting jaw.

The head of the stapler body may have two side walls perpendicular to the plane of the frame and provided with longitudinal slots adapted to interact with the webs of the frame so as to guide the stapler body.

It is expedient to have the side projections of the longitudinal slots of the stapler body different in length from each other on the same edge of the stapler body in such a manner that the height of the projections arranged towards the bottom of the slot in the supporting body be less than the depth of the recesses in the frame webs, while the height of the projections arranged towards the open slot end be in excess of the depth of said recesses.

It is also desirable that one of the walls of the stapler body head, that are arranged in parallel with the plane of the frame, be made detachable.

The wall of the stapler body head that faces the slot in the supporting body may have a notch open towards the detachable wall of the stapler body head.

The proposed surgical suturing instrument, unlike the known one, enables the application of mechanical sutures to tissues located in narrow deep cavities where there is less room for maneuvring with the instrument in the plane of the frame, be made detachable.

The wall of the stapler body head that faces the slot in the supporting body may have a notch open towards the detachable wall of the stapler body head.

The proposed surgical suturing instrument, unlike the known one, enables the application of mechanical sutures to tissues located in narrow deep cavities where there is less room for manoeuvring with the instrument in the plane of the frame and it is difficult to reach the place of suture application. Novel constructional arrangement of the instrument, whereby the supporting body is joined with the remainder of the instrument in the direction perpendicular to the plane of the frame, makes it unnecessary to have more room in the plane of the frame to assemble the supporting body with the remainder of the instrument.

Under conditions of restricted space in the operative wound for manoeuvring with the instrument and poor observability of the place of suturing, the above said novel feature of the instrument engenders a new technique of approaching the supporting jaw of the supporting body and the magazine to the tissues undergoing suturing. Said technique avoids any injury to the tissues undergoing suturing or the surrounding tissues. This technique consists in bring the supporting body into position by itself, separate from the remainder part of the instrument, whereupon the stapler body is inserted into the slot of the supporting body along with the other components, without any displacement of the unit with respect to the supporting body in the plane of the frame being necessary.

The proposed embodiment of the slot in the supporting body that allows the use of the aforesaid instrument application technique, makes practical the embodiment of the supporting body frame as a closed structure. This adds much to the constructional rigidity of the instrument as a whole, thereby ensuring a considerable reduction of the cross-sectional area of the supporting body frame elements (over three times as compared to the known instrument). This, in turn, provides for the possibility of an atraumatic introduction of the frame elements into a much narrower gap in between the tissues in the operative wound, involves less width of tissues necessary for setting the instrument into suturing position, increases the elasticity of the sutures applied and, with the width of the strip of tissues remaining the same, an increase in the lumen of the tube formed by suture application to the margins of the strip of tissues. All the aforesaid advantages improve the quality of sutures applied by the present instrument.

The aforelisted advantages of the proposed instrument over the known one are of especially great importance in the suturing of the pharynx which is necessary in the process of laryngectomy for cancer. The construction of the instrument enables the conglomerated tumor tissues to pass through the frame opening in the direction perpendicular to the plane of the frame of the supporting body detached from the remainder of the instrument without inflicting any injury upon the pharynx and the surrounding tissues, whereupon the remainder of the instrument is joined with the supporting body without the necessity of displacing the stapler body towards the chin or the breast, i.e., without dislodging the supporting body in the plane of the frame. This makes the method of mechanical suturing of the pharynx in a laryngectomy more practical.

As compared to the routine method of manual suturing of the walls of the pharynx in a laryngectomy, following the excision of the tumor to be removed, application of the proposed instrument reduces greatly the danger of infecting the operative wound and the pharynx with the contents of the tumor, since first, the walls of the pharynx are sutured and the lumen of the ablated portion is blocked with the use of a special clamp and only after this is done, the tumor being removed is excised together with the clamp along the instrument face and severed from the sutured pharynx. Application of the proposed instrument improves regeneration conditions of the tissues that generally are sutured after having been subjected to beam therapy. This considerably reduces the time of suture application to the pharynx and reduces postoperative complications.

BRIEF DESCRIPTION OF THE DRAWINGS

In what follows, the invention is illustrated in a specific embodiment thereof and the accompanying drawings, wherein:

FIG. 11 a, b, c, are a diagrammatic illustration of the successive steps of bringing the instrument into a suturing position and the interaction of the components of the suturing part of the instrument when a suture is placed on the throat walls during a laryngectomy.

DETAILED DESCRIPTION OF THE INVENTION

With reference to the accompanying drawings, the surgical suturing instrument comprises a supporting body 1 (FIGS. 1, 2) with a slot 2 and a flat frame 3. The frame 3 has a supporting jaw 4 arranged transversely with respect to the slot 2 and provided with a flat face 5 (FIG. 1) facing the slot 2. The flat face 5 of the supporting jaw 4 carries depressions to bend the staples (not shown). Mounted in the slot 2 of the supporting body 1 with the capacity to longitudinally traverse said slot is a stapler body 6 with a head 7 which accommodates a replaceable magazine 8 (FIGS. 1,3) with open-end slots for staples. Interconnected with the stapler body 6 with the capacity to longitudinally traverse said body staple ejector 9 (FIG. 3) provided with driving projections 10. The depressions in the supporting jaw 4, the respective slots in the magazine 8 and the staple driving projections 10 are arranged in the specific embodiment of the instrument, in two rows and serve largely for establishing oblong sutures. In a general case the any number of rows may be used.

The stapler body 6 has a tailpiece 11 with a male thread 12 to which is fitted a nut 13, and with a threaded hole 14 into which a screw 15 is fitted. The nut 13 is an actuator of the stapler body 6 and has an annular groove 16 to interact with the supporting body 1. The screw 15 is an actuator of the ejector 9 and has at its end an annular groove 17 with which is engaged a fork 18 (FIG. 4) provided on the ejector 9. At its other end the screw 15 (FIG. 3) has a hole 19 with longitudinal slots (not shown), into which hole, a detachable handle 20 is fitted, having projections 21 for interaction with the walls of the longitudinal slots of the hole 19 during rotation of the handle 20. When manipulating the instrument, the detachable handle 20 can be removed to preclude an inadvertent turn of the screw 15 of the ejector 9 and the premature ejection of the staples from the magazine 8.

The slot 2 (FIG. 1) in the supporting body 1 has its open end facing the direction perpendicular to the plane of the frame 3 of the supporting body 1 so as to provide for the stapler body 6 with the ejector 9 (FIG. 3) to be inserted into the slot 2 and extracted therefrom in said direction. A bottom 22 (FIG. 2) of the slot 2 of the supporting body 1 is parallel to the plane of the frame 3.

In the specific embodiment of the instrument, the frame 3 of the supporting body 1 is made closed. It is worth noting, however, that in a general case the frame may be shaped otherwise, e.g., as a hook.

Provision of the closed frame of the supporting body is expedient in view of a necessity to impart maximum rigidity to the construction of the instrument.

Figure 5:
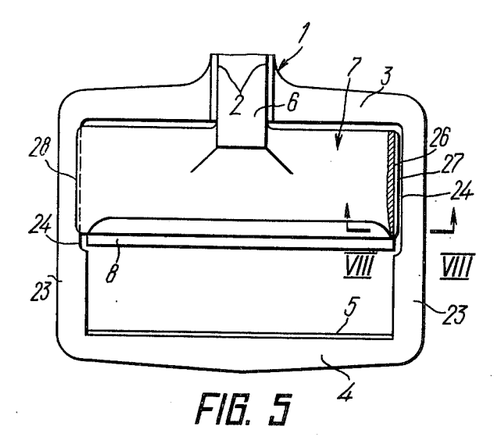
FIG. 5 is the head of the stapler body while in the initial position with respect to the supporting body frame, according to the invention.

The frame 3 of the supporting body 1 comprises two webs 23 parallel to the slot 2 and adapted to serve as guides for the head 7 (FIG. 1) of the stapler body 6. The rear portions of the webs 23 (with respect to the supporting jaw 4) are provided with recesses 24 (FIGS. 1, 5) which are commensurable in length with the head 7 of the stapler body 6 and are needed to provide for the stapler body 6 to be inserted into the slot 2 of the supporting body 1 and withdrawn therefrom when in the rearmost position with respect to the supporting jaw 4 of the frame 3 as illustrated in FIG. 5.

The head 7 of the stapler body 6 has two side walls 25 (FIG. 6) perpendicular to the plane of the frame 3 and provided with longitudinal slots 26 to interact with the webs 23 (FIG. 5) of the frame 3. The slots 26 (FIG. 6) stop the head 7 of the stapler body from any transversal displacement with respect to the supporting jaw (FIG. 5) of the frame 3, this being accomplished by side projections 27 and 28 (FIG. 7) of the slots 26 in the head 7 of the stapler body straddling the frame webs 23.

In its tail portion, the stapler body 6 (FIG. 1) comprises projections 29 which engage grooves 30 on the side walls of the slot 2 in the supporting body 1 and, along with the projections 27 and 28 (FIG. 7) of the head 7 of the stapler body, interconnect the stapler body 6 (FIG. 1) with the supporting body 1 when the former is in its forward working position with respect to the supporting jaw 4 of the frame 3.

Because the frame 3 of the supporting body 1 is made closed, when the slots 26 (FIG. 5) on the side walls of the head 7 of the stapler body are interconnected with the webs 23 of the frame 3, high rigidity of the instrument as a whole is attained which ensures stability of the mutual arrangement of the magazine 8 (FIG. 1) and the supporting jaw 4 under the maximum load upon the instrument corresponding to the moment of staple deformation. This enables the cross-sectional area of the frame elements to be reduced several times as compared to the known surgical instruments of the same type, with the retained stability of the staple deformation process and high-quality sutures obtained.

Figure 8:
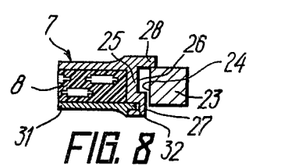
FIG. 8 is a section taken along the line VIII—VIII in FIG. 5.

The height of the projections 27 (FIGS. 5, 8) arranged towards the bottom 22 (FIG. 2) of the slot 2 of the supporting body 1 is less than the depth of the recesses 24 (FIGS. 5, 8) in the webs 23, while the height of the projections 28 arranged towards the open end of the slot 2 (FIG. 8) exceeds the depth of the recesses 24. This makes it possible to fit the head 7 of the stapler body onto the webs 23 of the frame 3 of the supporting body 1, when assembling the instrument, and to avoid placing the entire head 7 of the stapler body into the clear opening of the frame 3, whereby the instrument assembly is rendered convenient and any misassembly is excluded.

Figures 1, 3, 4:
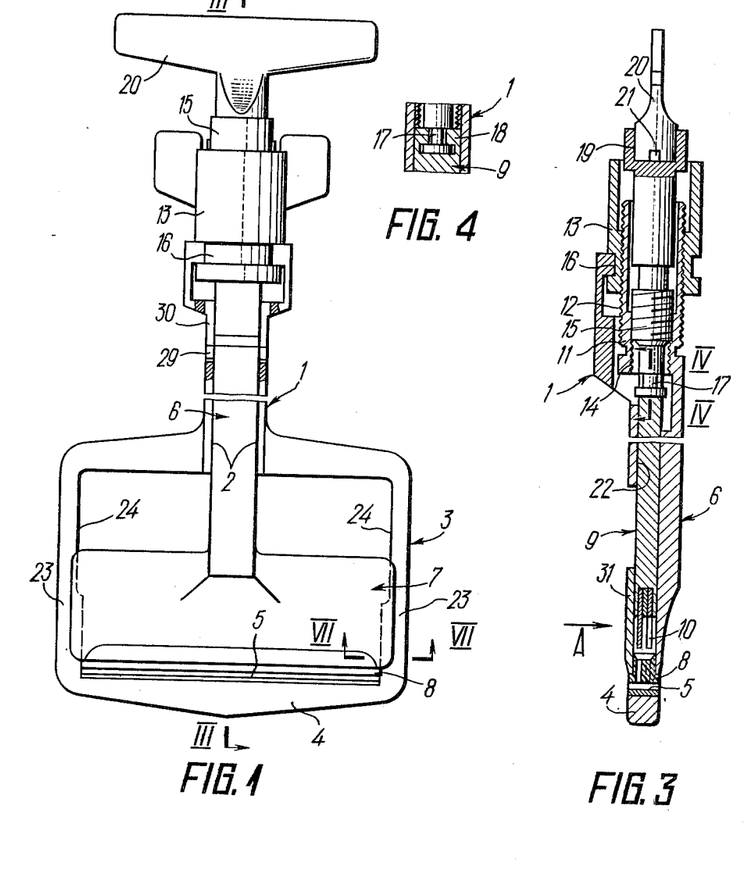
FIG. 1 is a partially cutaway elevational view of a surgical suturing instrument, according to the invention.
FIG. 3 is a section taken along the line III—III in FIG. 1.
FIG. 4 is a section taken along the line IV—IV in FIG. 3.
Figure 2:
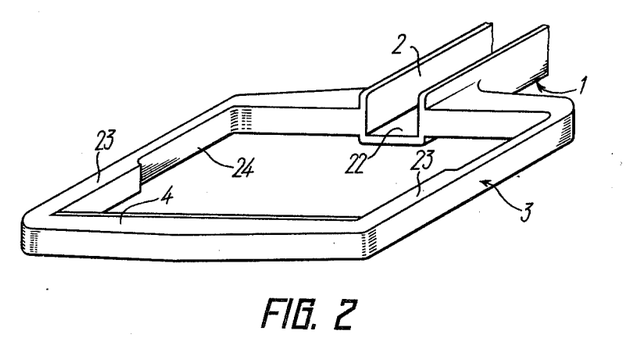
FIG. 2 is a portion of the supporting body, according to the invention.
Figure 6:
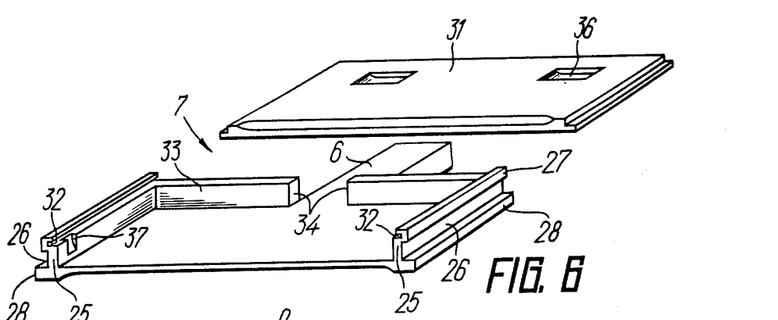
FIG. 6 is the head of the stapler body with a detachable wall, according to the invention.
Figure 7:
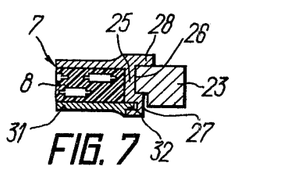
FIG. 7 is a section taken along the line VII—VII in FIG. 1.
Figure 9:
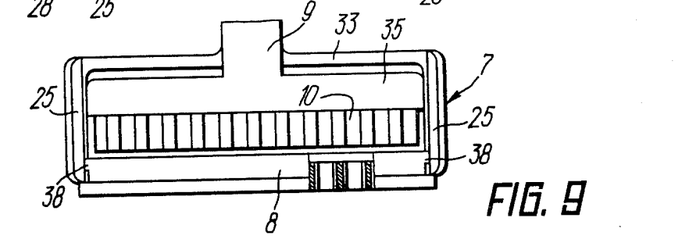
FIG. 9 is a view along the arrow A of FIG. 3 with the detachable wall of the stapler body head out of position.

A wall 31 (FIGS. 6–8) of the head 7 of the stapler body, arranged in parallel with the plane of the frame, is made detachable and is fitted into longitudinal slots 32 made on the inside surfaces of the side walls 25 till it thrusts against the magazine 8 (FIG. 3). A wall 33 (FIG. 6) of the head 7 of the stapler body, facing the slot 2 (FIG. 1) of the supporting body 1, has a notch 34 (FIG. 6) which opens towards the detachable wall 31 of the head 7. This makes the assembly of the ejector 9 (FIG. 3) and the stapler body 6 convienent. The ejector 9 (FIG. 9) passes through the notch 34 (FIG. 6) in the wall 33, whose head 35 and the magazine 8 are located between the side walls 25 of the head 7 of the stapler body and is locked in position in the head 7 by means of the detachable wall 31 (FIG. 6). The wall 31 also makes it easy to replace the magazine 8 (FIG. 9) for which purpose said wall is drawn out to release the magazine 8 and extract it from the head 7 of the stapler body. To make the wall 31 (FIG. 6) easier to draw out, depressions 36 are provided on the outside surface thereof. With the wall 31 removed, the head 7 of the stapler body is exposed on the side of its broadest surface, while the inside space confined between the side walls 25 is of a relatively small depth which makes it easier to clean the head 7 of the stapler body.

Transverse grooves 37 are on the inside surfaces of the side walls 25 of the head 7 of the stapler body, into which grooves projections 38 (FIG. 9) of the magazine 8 are fitted for locking the latter into the stapler body 8 in the direction of the axis of the slot 2 (FIG. 1) in the supporting body 1.

Now let us consider the operation of the instrument with reference to the operation of laryngectomy for cancer. With the supporting body 1 detached from the test of the instrument (FIGS. 10 and 11a), the supporting jaw 4 of the frame 3 of the supporting body 1 is positioned close to the sound portions of the wall of the pharynx that are to be sutured, having passed through the clear opening of the frame 3 the comglomerate of tumor tissues prepared for resection, along with the larynx. The frame 3 (FIG. 11a) of the supporting body 1 in this case is brought into position to the tumor from above with respect to the patient in the recumbent position in such a way that the side webs 23 of the frame 3 are introduced into the incisions in the tissues in the area of the root of the tongue and the trachea, while the slot 2 in the supporting body 1 is positioned thereabove. Then the head 7 (FIGS. 10 and 11b) of the stapler body 6 is introduced into the enlarged portion of the opening of the frame 3 of the supporting body 1 until the projections 28 contact the side webs 23 of the frame 3, whereupon the stapler body 6 is inserted into the longitudinal slot 2 of the supporting body 1.

Upon bringing the petal of the epiglottis out of the zone confined between the supporting jaw 4 and the magazine 8, both of them are brought together. The proper suturing gap is obtained by rotating the nut 13 (FIGS. 1, 3) of the actuator of the stapler body 6, with the result that the projections 27 and 28 (FIGS. 5 and 7) of the side walls of the head 7 straddle the side webs 23 of the frame 3 and reliably fix the magazine 8 in working position with respect to the supporting jaw 4, the projections 29 (FIGS. 1 and 10) of the stapler body 6 engaging the grooves 30 in the side walls of the slot 2 of the supporting body 1.

Figure 11A:
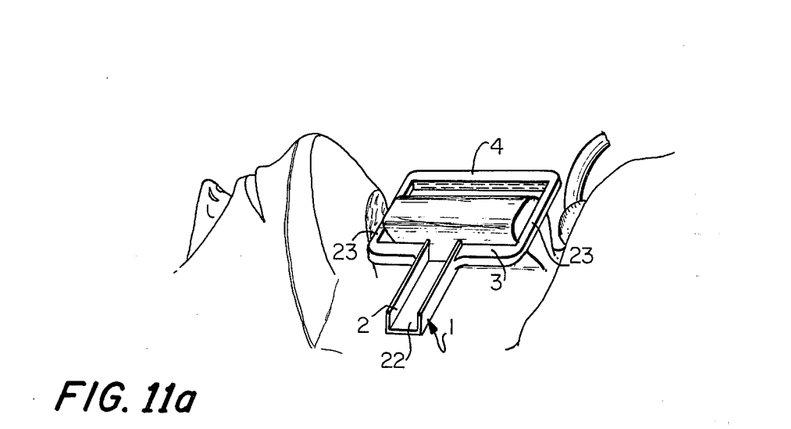
Figure 11B:
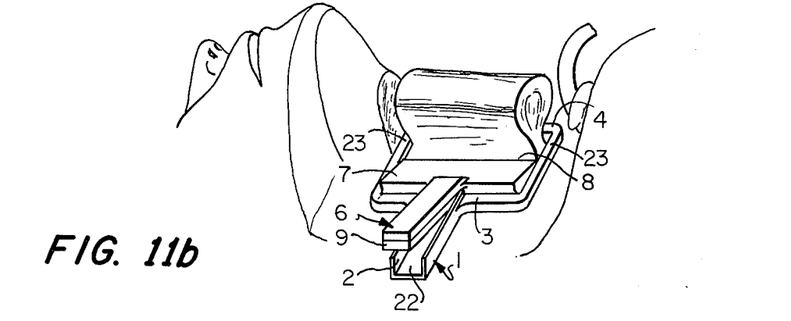
Figure 11C:
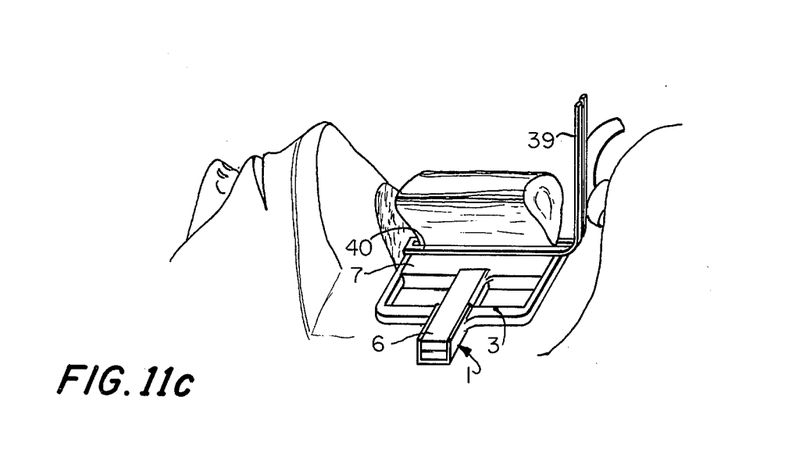

The walls of the pharynx are sutured by rotating the handle 20 (FIG. 3) of the screw 15 of the actuator of the ejector 9, the movement of which results in the driving projections 10 entering the respective slots in the magazine 8 and ejecting the staples therefrom. Upon suturing, a special clamp 39 (FIG. 11c) in place under the tumor to be resected until it contacts the instrument, and the tissues between the jaws 40 of the clamp 39 and the instrument are severed with a scalpel. Next the magazine 8 (FIGS. 1 and 3) is withdrawn from the supporting jaw 4 of the frame 3 of the supporting body 1 by rotating the nut 13 in the reverse direction, and the instrument is removed from the operative wound.

Figure 10:
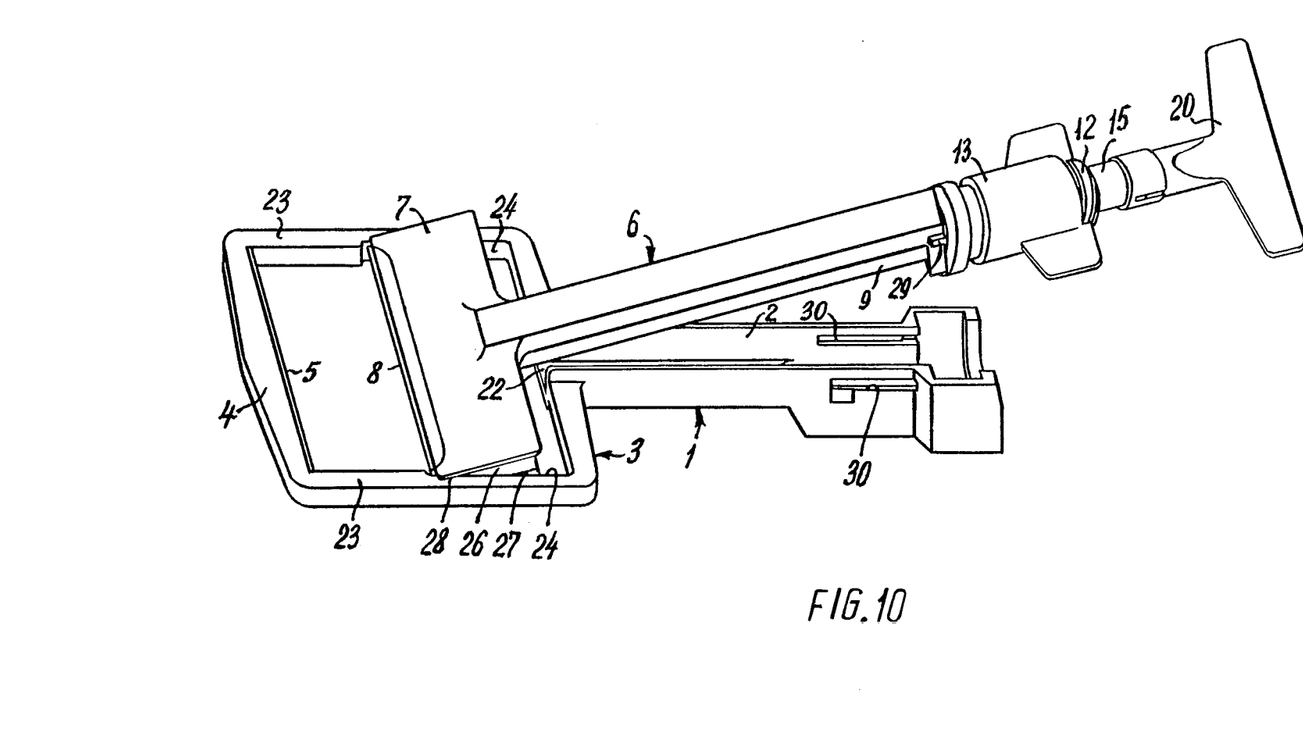
FIG. 10 is a perspective view of the surgical suturing instrument according to the invention, the supporting body thereof being shown in a horizontal position, and the rest of the instrument being shown at an angle to the supporting body at the moment when it is being joined thereto or disconnected therefrom.

In order to extract the stapler body 6 together with the staple ejector 9 from the supporting body, 1, the nut 13 is screwed on the outer thread 12 in the tail portion of the stapler body 6, as shown in FIG. 10, in which case the side projections 27 of the head 7 of the stapler body 6 are disengaged from the webs 23 (FIGS. 5 and 8) of the frame 3 of the supporting body 1, while the projections 29 (FIGS. 1 and 10) of the stapler body 6 are disengaged from the grooves 30 (FIGS. 1 and 10) of the supporting body 1. In the resulting position, the stapler body 6 and the staple ejector 9 are easily extracted from the supporting body 1 (FIG. 10). The position of the ejector 9 relative to the stapler body 6, predetermined by the position of the screw 15 in the threaded hole 14, is unimportant during the extraction of the stapler body 6 together with the ejector 9 from the supporting body 1.

In some cases of instrument application in the thoracic or abdominal cavity, e.g., in suturing pulmonary tissues, it is useful to introduce the instrument into the operative wound in an assembled state, as is usually the case when using the known instruments. When the frame of the supporting body of the instrument, according to the invention, is hook-shaped, the application technique of the instrument in all cases listed above differs in nothing from the application of the known instrument. If, on contrary, the frame of the supporting body of the instruments is made closed, the tissues undergoing suturing are introduced between the side webs 23 of the frame 3 of the supporting body 1 (FIG. 5) and the supporting jaw 4 and the magazine 8 when retracted with respect to the supporting jaw 4.

What is claimed is:

1. A surgical instrument for suturing tissues and organs with metal staples, comprising:
   a supporting body with a longitudinal slot;
   a flat frame extending from one end of said supporting body and having a supporting jaw disposed transversely with respect to said slot, said supporting jaw having a flat face facing said slot, said flat face having depressions for the legs of said staples to be bent;
   a stapler body disposed in said slot of said supporting body and attached thereto for reciprocating longitudinal movement therein, said stapler body having a head at one end thereof toward said supporting jaw; a magazine for said staples disposed within said head of said stapler body toward said supporting jaw;
   a staple ejector attached movably to said stapler body and adapted to reciprocate longitudinally in said stapler body for ejecting staples from said magazine;
   an actuator means for said stapler body connected at the opposite end of said stapler body from said head, for controlling the longitudinal movement of said stapler body in said slot of said supporting body toward and away from said supporting jaw;
   an actuator of said staple ejector connected at the end of said stable ejector farthest from said staple magazine for reciprocating said staple ejector relative to said magazine; said slot in said supporting body being open in the direction perpendicular to the plane of said flat frame of said supporting body whereby said stapler body with said staple ejector and said staple magazine can be inserted inside and removed from said slot in said direction, thereby enabling the placement of said supporting jaw of said supporting body, separated from said stapler body, in a difficulty accessible suturing position and the subsequent attachment of said stapler body to said supporting body in said direction.

2. The surgical instrument as claimed in claim 1, wherein said frame of the supporting body is made in a closed configuration having two webs connecting said supporting jaw to said supporting body; said webs of said frame being parallel to said slot in the supporting body and serving as guides for said head of the stapler body; said webs provided with recesses located in their rear portions with respect to said supporting jaw, said recesses being commensurate in length with said head of the stapler body and adapted to provide for said stapler body with the staple ejector to be inserted into said slot in the supporting body and extracted therefrom only when in the rearmost position with respect to said supporting jaw.

3. The surgical instrument as claimed in claim 2, wherein said head of the stapler body has two side walls perpendicular to the plane of said frame and provided with longitudinal slots adapted to interact with said webs of the frame so as to guide said stapler body.

4. The surgical instrument as claimed in claim 3, wherein said head of the stapler body has a detachable wall arranged in parallel with the plane of said frame.

5. The surgical instrument as claimed in claim 4, wherein said head of the stapler body has a wall arranged perpendicular to the plane of said frame and facing said slot, said wall being provided with a notch open towards said detachable wall of said head of the stapler body.

6. The surgical instrument as claimed in claim 3, wherein side projections which define the side walls of said longitudinal slots in said head of the stapler body are different in height so that the height of said side projections on the side surface facing toward the bottom of said slot in the supporting body is smaller than the depth of said recesses in said frame webs, allowing said head of the stapler body to be freely introduced into the open end of said frame of the supporting body, while the height of said side projections on the side surface facing away from the bottom of said slot in the supporting body is greater than the depth of said recesses, preventing said head of the stapler body from passing through the open end of said frame when said stapler body is attached to said supporting body during operation and ensuring easy connection of the stapler body to the supporting body.

7. The surgical instrument as claimed in claim 6, wherein said head of the stapler body has a detachable wall arranged in parallel with the plane of said frame.

8. The surgical instrument as claimed in claim 7, wherein said head of the stapler body has a wall arranged perpendicular to the plane of said frame and facing said slot, said wall being provided with a notch open towards said detachable wall of said head of the stapler body.

* * * * *